(12) United States Patent
McNally et al.

(10) Patent No.: US 6,340,469 B1
(45) Date of Patent: Jan. 22, 2002

(54) SYSTEM FOR PROPHYLACTIC TREATMENT OF MAMMARY DISORDERS

(75) Inventors: Vincent McNally, Sandyford; James Patrick Morgan, deceased, late of Bellinter, both of (IE), by Bridie Morgan, legal representative

(73) Assignee: Bimeda Research and Development LTD (IE)

( * ) Notice: Subject to any disclaimer, the term of this patent is extended or adjusted under 35 U.S.C. 154(b) by 0 days.

(21) Appl. No.: 09/694,676

(22) Filed: Oct. 24, 2000

Related U.S. Application Data

(63) Continuation of application No. 09/319,544, filed on Aug. 10, 1999, now Pat. No. 6,254,881.

(30) Foreign Application Priority Data

Dec. 18, 1996 (IE) ................................................. 960896

(51) Int. Cl.$^7$ ................................................. A23K 1/18
(52) U.S. Cl. ........................ 424/438; 604/74; 604/500; 604/514; 514/503
(58) Field of Search ............................ 424/438; 604/74, 604/500, 514

(56) References Cited

U.S. PATENT DOCUMENTS

| | | | | |
|---|---|---|---|---|
| 3,912,806 A | | 10/1975 | Dowrick et al. ............... 424/16 |
| 4,049,830 A | | 9/1977 | Pugliese ....................... 424/343 |
| 4,172,138 A | * | 10/1979 | Rhodes ........................ 424/271 |
| 4,344,967 A | | 8/1982 | Easton et al. ................ 424/359 |
| 5,195,966 A | * | 3/1993 | Corby .......................... 604/75 |
| 5,593,384 A | * | 1/1997 | Halem ......................... 604/514 |
| 6,107,344 A | * | 8/2000 | Loosemore .................. 514/635 |

FOREIGN PATENT DOCUMENTS

| | | | |
|---|---|---|---|
| EP | 0271306 | 6/1988 | ................. 424/16 |
| GB | 1441747 | 7/1976 | ................. 424/19 |
| GB | 2273441 | 6/1994 | ................. 424/342 |
| WO | 9413261 | 6/1994 | |

* cited by examiner

*Primary Examiner*—James H. Reamer
(74) *Attorney, Agent, or Firm*—Rothwell, Figg, Ernst & Manbeck, P.C.

(57) ABSTRACT

An antiinfective-free formulation for prophylactic treatment of mastitis in dry cows comprises a seal formulation having approximately 65% by weight of bismuth sub-nitrate in a gel based on aluminum stearate. The seal formulation is prepared by adding the bismuth sub-nitrate to the gel base in at least two separate stages.

8 Claims, No Drawings

SYSTEM FOR PROPHYLACTIC TREATMENT OF MAMMARY DISORDERS

This application is a continuation of application Ser. No. 09/319,544, filed on Aug. 10, 1999 U.S. Pat. No. 6,254,881.

The invention relates to a veterinary composition, particularly for the prophylactic treatment of mastitis in cows.

Bacterial infection via the teats of a cow is the most common cause of mastitis.

It is known to treat teats of a cow with a long acting antibiotic in a slow release form with effective cover only being provided whilst minimum inhibitory concentration (MIC) levels of the antibiotic are maintained. This period of cover can vary from 4 to 10 weeks.

It is also known to infuse a cloxacillin-based antibiotic into the udder following the last lactation and before the cow is dried off, immediately followed by a seal formulation to seal the teat canal.

The invention is directed towards providing an improved veterinary composition, particularly for the prophylactic treatment of mastitis in dry cows.

STATEMENTS OF INVENTION

We have found that if a physical barrier is provided within the teat canal and/or the lower teat sinus during the dry period without the use of antibiotics, the incidence of mammary disorders is substantially reduced. This is very surprising as all conventional treatments involve the use of antibiotics. Because no antibiotics are required very substantial advantages result, without any significant reduction in effectiveness.

According to the invention there is provided an antiinfective-free formulation for prophylaxis of intramammary infection comprising a seal formulation to provide a physical barrier in the teat canal.

This non-antibiotic approach to preventing new dry period infection in dairy cows has major potential for the dairy industry as it results in the reduction of the incidence of antibiotic contamination in early season milk production. Thus the invention provides a quality improvement to dairy production and will facilitate farmers meeting consumer preferences for reducing the level of antibiotics used in food production.

According to another aspect the invention provides an antiinfective-free method of prophylactic treatment of mammary disorders in non-human animals during an animals' dry period by sealing the teat canal with a seal formulation to provide a physical barrier in the teat canal.

The invention also provides a prophylactic method of controlling the infection of the mammary gland by a mastitis-causing organism by sealing the gland with a seal formulation to provide a physical barrier in the teat canal.

In a particularly preferred embodiment of the invention the seal formulation comprises a non-toxic heavy metal salt in a gel base. Preferably, the heavy metal salt is present in an amount of between 50% and 75% by weight, most preferably approximately 65% by weight. We have found that these are the optimum levels of heavy metal salt to achieve an effective seal.

In a preferred embodiment of the invention the heavy metal salt is bismuth sub-nitrate. This is a particularly useful non-toxic heavy metal salt.

In one embodiment of the invention the base is a gel based on aluminum stearate. Preferably, in this case, the gel includes a vehicle such as liquid paraffin. This formulation has effective processing and use properties.

In another embodiment of the invention the gel comprises a polyethylene gel. The gel may be based on low density polyethylene or on high density polyethylene.

The invention also provides a veterinary composition for use in the prophylactic treatment of mammary disorders in non-human animals during an animals' dry period.

According to a further aspect the invention provides a process for preparing a seal formulation comprising the steps of adding a non-toxic heavy metal salt to a gel base in at least two separate stages. This process is particularly effective for producing the preferred seal formulation of the invention.

Preferably, a first portion of heavy metal salt is added to a gel base in a first stage and a second portion of the heavy metal salt is added to the gel base containing the first portion of the heavy metal salt.

In this case preferably the weight ratio of the second portion of the heavy metal salt to the first portion of the heavy metal salt is at least 1:1, most preferably approximately 2:1.

DETAILED DESCRIPTION OF THE INVENTION

The invention will be more clearly understood from the following description thereof given by way of example only.

EXAMPLE 1

Raw Materials
Liquid Paraffin B.P.434.8 Kg
Alugel 30 DF (Sterile) 69.2 Kg
Bismuth Sub-Nitrate936.0 Kg
B.P.C. (Sterile)

To prepare a batch of seal formulation the liquid paraffin is first delivered into a Skerman 800L kettle. The mixer is run at 20 RPM. The Alugel 30 DF (aluminum stearate) is then added through the transfer port. The mixer is turned off between additions of the Alugel powder. The steam line is opened and the temperature is allowed to rise to 160 to 165° C. This temperature is held for approximately 2 hours to sterilize the mixture. At the end of the sterilizing cycle, the condensate valve is opened and blown down. Cooling water is then allowed into the jacket to cool the contents to less than 40° C. The base thus formed is then checked for quality. If necessary, the batch base may be homogenized for 10 minutes using a Silverson Homogeniser.

The charge port is then opened and 296 kg of the bismuth sub-nitrate is added in 10 kg lots. The contents are mixed for one minute at 20 RPM between additions of each 10 kg of bismuth sub-nitrate. Mixing is continued for approximately 1 hour at 45 RPM.

The remaining 640 Kg of bismuth sub-nitrate is then added in 10 Kg lots as above and mixing is continued for 1 hour following the final additions.

We have found that the addition of the bismuth sub-nitrate in two separate portions is important in producing a seal which can be processed and used effectively.

If necessary, the mixture is homogenized for 15 minutes using a Silverson Homogeniser.

The product is then transferred to a Colibri filling machine for filling into injector tubes.

EXAMPLE 2

5 Cows were infused in all four quarters at drying off with the seal formulation prepared as described in Example 1. These cows had previously been determined as uninfected in all four quarters.

Commencing at the first milking after calving, these cows were milked and the composite milk sample collected for analysis. This process was repeated for the first 10 milkings after calving. Milk samples were also collected in the same manner from 5 untreated cows.

To simulate the milk handling process within the milking system, these milk samples were passed through a fibre filter material used in milking machine filters. The milk samples were then analyzed by mass spectrometry for bismuth concentration.

The average bismuth level in milk drawn at first milking was 3.3 ppm declining to 0.39 ppm at milking No. 10. The maximum level recorded for any individual cow was 8 ppm at first milking. For untreated cows the levels fluctuated in the range 0.001 to 0.03 ppm.

The seal formulation described in Example 1 was administered at drying off and has been shown to reduce the incidence of new infection in the dry cow period and in the period around calving. This reduction appears to be comparable with that achieved by prophylactic antibiotic treatment. Thus, the seal of the invention very surprisingly offers a non-antibiotic approach to dry cow period prophylaxis.

EXAMPLE 3

Evaluation of seal of Example 1.

4 Mastitis-free cows selected at drying off.
2 Teats in each cow infused at drying-off with seal and remaining teats untreated (day 0).
8 Teats sealed and 8 teats untreated (controls).
3 Days later (day 3) all teats were inoculated into the teat canal (depth of 4 mm; using 22 cfu of Streptococcus dysgalactiae code M and an inoculum volume of 0.1 ml).
New infections resulting from use of the inoculum occurred in five (5) of the untreated quarters in the period day 3 to day 13.
New infections resulting from use of the inoculum occurred in two (2) of the treated quarters in the period day 3 to day 13.
Resulting new infections were monitored daily for 10 consecutive days after inoculation (to day 13).
Samples of secretion were collected in an aseptic manner from quarters showing signs of clinical mastitis prior to treatment with antibiotics.
All quarters in all 4 cows were sampled in an aseptic manner on day 13 (the last day of the trial)—these samples were used to:
  (1) check the amount of seal remaining in teats
  (2) monitor the level of Str. dysgalactiae surviving in the teats after 10 days Clinical Infection Results:

| CFU/ml | Inoculation Depth | Control | Seal |
|---|---|---|---|
| 22 | 4 mm | 5[a]/8[b] 63% | 2[a]/8[b] 25% |

[a]Number of new infections
[b]Number of quarters challenged with Str. dysgalactiae

EXAMPLE 4

Evaluation of seal of Example 1.
17 Mastitis-free cows* selected at drying off.
2 Teats in each cow infused at drying-off with seal and remaining teats untreated (day 0).
32 Teats sealed and 32 teats untreated (controls).
3 Days later (day 3) all teats were inoculated into the teat canal (depth of 17 mm; using 1,190 cfu of Streptococcus dysgalactiae code M and an inoculum volume of 0.1 ml).
New infections resulting from use of the inoculum occurred in twenty (20) of the untreated quarters in the period day 3 to day 13.
New infections resulting from use of the inoculum occurred in eight (8) of the treated quarters in the period day 3 to day 13.
Resulting new infections were monitored daily for 10 consecutive days after inoculation (to day 13).
Samples of secretion were collected in an aseptic manner from quarters showing signs of clinical mastitis prior to treatment with antibiotics.
All quarters in all 17 cows were sampled in an aseptic manner on day 13 (the last day of the trial)—these samples were used to:
  (1) check the amount of seal remaining in teats
  (2) monitor the level of Str. dysgalactiae surviving in the teats after 10 days.

Clinical Infection Results:

| CFU/ml | Inoculation Depth | Control | Seal |
|---|---|---|---|
| 1,190 | 17 mm | 20[a]/32[b] 63% | 8[a]/32[b] 25% |

[a]Number of new infections
[b]Number of quarters challenged with Str. dysgalactiae
*A total of 4 quarters were infected in three cows and these quarters were excluded from the study. Therefore 32 quarters were assigned to each treatment.

EXAMPLE 5

A total of 528 cows in three commercial herds were used. Each herd had a general history of dry period mastitis. The breed of the herds was predominantly Fresian or Fresian crosses.

Cows with at least three uninfected quarters, immediately prior to drying off, were identified within the three herds. All individual quarters were assumed to be independent units. The treatments used were as follows 1. Negative Control-Untreated, no infusions at drying off, but teat ends were sanitized with alcohol soaked cotton wool swabs.

2. Positive Control-treated with 250 mg cephalonium in a long-acting base, infused at drying off. This product is known as CEPRAVIN DRYCOW. Cepravin is a trademark of Mallinckrodt Veterinary.

3. Antibiotic with Seal-Cloxacillin benzathine 600 mg in a 4 g unit dose infused at drying off and followed immediately by an infusion of 4 g of a blend of bismuth sub-nitrate (66%) in liquid paraffin with 8.5% Alugel 30DF.

4. Seal-Bismuth sub-nitrate 66% w/w in liquid paraffin with 8.5% alugel 30 DF in a unit dose of 4g infused at drying off.

These treatments were randomized among the 528 cows determined to have three or four uninfected quarters at drying off. The treatments were randomized between quarters to achieve as far as possible the same number of quarters per treatment, left and right, front and back.

Bacteriological results for individual quarters at drying off and at calving were compared to calculate the incidence of new intramammary infections (IMI). Chi-square testing was used to compare the incidence of new infection between quarters, treatments and controls.

The results of the treatments are summarized in Table 1.

This experiment has demonstrated that the antiinfective-free seal formulation of the invention administered at drying off is very surprisingly equivalent in terms of prophylactic efficacy, to a long acting dry cow antibiotic. All three treatments reduced new IMI during the dry period by approximately 85%. Surprisingly, there was no significant difference between the antibiotic based treatments and the antibiotic-free treatment of the invention. Thus, this study has shown that by physically sealing the teat canal with a seal which has no bacteriostatic or bacterial action, the dry period IMI may, surprisingly, be controlled. The invention has the potential therefore of achieving dry period prophylaxis on a wide scale, at a lower unit cost, and with no risk of antibiotic residues after calving.

The invention is not limited to the embodiments hereinbefore described which may be varied in detail.

TABLE I

New intrammary infections (IMI) identified during the study, grouped by period and by herd.

Number of new IMI (quarters)

| | 1. Negative controls | | | 2. Positive controls | | | 3. Antibiotic + Seal | | | 4. Seal | | |
|---|---|---|---|---|---|---|---|---|---|---|---|---|
| Herd ID | 1 | 2 | 3 | 1 | 2 | 3 | 1 | 2 | 3 | 1 | 2 | 3 |
| Total no quarters | 249 | 141 | 138 | 249 | 141 | 138 | 249 | 141 | 139 | 249 | 141 | 138 |
| DRY PERIOD | | | | | | | | | | | | |
| Clinical IMI | 10 | 6 | 2 | 0 | 1 | 1 | 1 | 1 | 0 | 1 | 0 | 0 |
| CALVING IMI | | | | | | | | | | | | |
| Strep. spp. | 25 | 21 | 4 | 0 | 4 | 1 | 2 | 1 | 1 | 2 | 2 | 0 |
| S. aureus | 1 | 2 | 0 | 0 | 0 | 0 | 0 | 0 | 0 | 0 | 1 | 0 |
| Coag. Neg. staph. | 2 | 0 | 4 | 0 | 0 | 1 | 1 | 0 | 1 | 4 | 0 | 2 |
| Coliforms | 1 | 2 | 1 | 1 | 2 | 1 | 1 | 0 | 0 | 0 | 1 | 0 |
| Other organisms | 0 | 2 | 0 | 1 | 1 | 0 | 0 | 1 | 0 | 0 | 0 | 0 |
| Clinical, no growth | 1 | 1 | 0 | 0 | 0 | 0 | 0 | 0 | 0 | 0 | 0 | 0 |
| Total calving IMI | 30 | 28 | 9 | 2 | 7 | 3 | 4 | 2 | 2 | 6 | 4 | 2 |
| Total IMI | 40 | 34 | 11 | 2 | 8 | 4 | 5 | 3 | 2 | 7 | 4 | 2 |
| Overall IMI rate (%) | 16.1 | 24.1 | 8.0 | 0.8 | 5.7 | 2.9 | 2.0 | 2.1 | 1.4 | 2.8 | 2.8 | 1.4 |
| Total IMI across herds & periods | | | | | | | | | | | | |
| Strep. Spp. IMI | | $68^a$ | | | $7^b$ | | | $6^b$ | | | $5^b$ | |
| Other paths IMI | | $17^c$ | | | $7^d$ | | | $4^d$ | | | $6^d$ | |
| All paths IMI | | $85^f$ | | | $14^g$ | | | $10^g$ | | | $13^g$ | |
| Total quarters | | 528 | | | 528 | | | 528 | | | 528 | |
| Overall new IMI Rate | | 16.1% | | | 2.7% | | | 2.5% | | | 1.9% | |

(Within a row, values with differing superscripts are significantly different)

What is claimed is:

1. A system for forming an anti infective-free physical barrier in the teat canal of a non-human animal for prophylactic treatment of mammary disorders during the animal's dry period, said system consisting essentially of an anti infective-free seal formulation and an injector tube for infusing the seal formulation into the teat of the animal.

2. A formulation as claimed in claim 1 wherein the seal formulation comprises a non-toxic heavy metal salt in a gel base.

3. A formulation as claimed in claim 2 wherein the seal formulation contains at least 40% by weight of the heavy metal salt.

4. A formulation as claimed in claim 3 wherein the seal formulation contains from 50% to 75% by weight of the heavy metal salt.

5. A formulation as claimed in claim 4 wherein the seal formulation contains approximately 65% by weight of the heavy metal salt.

6. A formulation as claimed in claim 2 wherein the salt is bismuth sub-nitrate.

7. A formulation as claimed in claim 1 wherein the base is a gel based on aluminum stearate.

8. A formulation as claimed in claims 1 wherein the base includes liquid paraffin as a vehicle.

* * * * *